(12) United States Patent
Tam et al.

(10) Patent No.: US 10,093,787 B2
(45) Date of Patent: Oct. 9, 2018

(54) POLYMERIC WAVEGUIDE WITH SINGLE DOPANT

(71) Applicant: The Hong Kong Polytechnic University, Hong Kong (HK)

(72) Inventors: Hwa-Yaw Tam, Hong Kong (HK); Julien Bonefacino, Hong Kong (HK); Xin Cheng, Hong Kong (HK)

(73) Assignee: The Hong Kong Polytechnic University, Hong Kong (HK)

( * ) Notice: Subject to any disclaimer, the term of this patent is extended or adjusted under 35 U.S.C. 154(b) by 0 days.

(21) Appl. No.: 15/240,969

(22) Filed: Aug. 18, 2016

(65) Prior Publication Data

US 2018/0051161 A1    Feb. 22, 2018

(51) Int. Cl.
| | | |
|---|---|---|
| *G02B 6/00* | (2006.01) |
| *C08K 5/372* | (2006.01) |
| *G02B 6/02* | (2006.01) |
| *A61B 5/00* | (2006.01) |
| *G02B 6/122* | (2006.01) |
| *A61B 90/00* | (2016.01) |
| *G02B 6/12* | (2006.01) |

(52) U.S. Cl.
CPC ............ *C08K 5/372* (2013.01); *A61B 5/0059* (2013.01); *G02B 6/02033* (2013.01); *G02B 6/02114* (2013.01); *G02B 6/1221* (2013.01); *A61B 2090/3614* (2016.02); *D10B 2321/08* (2013.01); *G02B 2006/12166* (2013.01)

(58) Field of Classification Search
CPC .................. C08K 5/372; A61B 5/0059; A61B 2090/3614; G02B 6/02033; G02B 6/02076; G02B 6/02114; G02B 6/1221

USPC ................. 385/141–145; 526/286, 289, 313
See application file for complete search history.

(56) References Cited

U.S. PATENT DOCUMENTS

| | | | |
|---|---|---|---|
| 3,328,368 A | 6/1967 | Wang | |
| 5,509,505 A * | 4/1996 | Steger | B66B 1/40 187/393 |
| 6,256,139 B1 * | 7/2001 | Fujii | H01S 3/06708 359/341.1 |
| 6,653,425 B1 * | 11/2003 | Armstrong-Poston | C08F 12/34 526/286 |
| 6,800,424 B2 * | 10/2004 | Xu | C08F 22/18 385/122 |
| 7,491,441 B2 * | 2/2009 | Pokorny | C08F 222/1006 428/323 |

(Continued)

FOREIGN PATENT DOCUMENTS

| | | |
|---|---|---|
| CN | 101923287 A | 12/2010 |
| EP | 1291679 A1 | 3/2003 |

OTHER PUBLICATIONS

Wikipedia article "Diphenyl disulfide", available online since Jan. 31, 2012.*

(Continued)

*Primary Examiner* — Robert Tavlykaev
(74) *Attorney, Agent, or Firm* — Seed IP Law Group LLP

(57) ABSTRACT

The present invention relates to the use of dopants for polymer optical fibers or polymer waveguides containing the dopants, sensors in the polymer optical fibers or polymer waveguides, which may be used in the biomedical industry for the measurement of different physiological and physical variables.

16 Claims, 10 Drawing Sheets

(56) References Cited

U.S. PATENT DOCUMENTS

| | | | | |
|---|---|---|---|---|
| 2003/0132536 A1* | 7/2003 | Zhen | ............... | D01F 8/10 264/1.29 |
| 2004/0067000 A1* | 4/2004 | Bates | ............... | A61B 5/0097 385/7 |
| 2004/0101782 A1* | 5/2004 | Gorczyca | ............... | G02B 3/0056 430/290 |
| 2004/0197061 A1* | 10/2004 | Ogura | ............... | B29D 11/00721 385/123 |
| 2005/0018988 A1* | 1/2005 | Shih | ............... | G02B 6/1221 385/129 |
| 2008/0124508 A1 | 5/2008 | Sato | | |

OTHER PUBLICATIONS

"Holographic gratings in photosensitive acrylic polymers with high refractive index diphenyl sulfide" by Liu et al, Journal of Polymer Research, vol. 11, pp. 43-51, 2004.*

"Some observations on the photoproduct in benzenethiol, diphenyl disulfide, and diphenyl sulfide" by Russell, Journal of Physical Chemistry, vol. 79, No. 14, pp. 1353-1359, 1975.*

"Formation of the refractive index profile in the graded index polymer optical fiber for gigabit data transmission" by Ishigure et al, Journal of Lightwave Technology, vol. 15, No. 11, pp. 2095-2100, 1997.*

Bonefacino et al., "Recent Progress I Polymer Optical Fiber Light Sources and Fiber Bragg Gratings," *IEEE J. Sel. Topics Quantum Electron.* 23(2): 5600911, 2017. (11 pages).

Girschikofsky et al., "Optical planar Bragg grating sensor for real-time detection of benzene, toluene and xylene in solvent vapour," *Sensors and Actuators* B 171-172: 338-342, 2012.

Peng et al, "Dye-Doped Step-Index Polymer Optical Fiber for Broadband Optical Amplification," *J. Lightwave Tech.* 14(10): 2215-2223, 1996.

Rosenberger et al., "Planar Bragg grating in bulk Polymethylmethacrylate," *Opt. Express* 20(25): 27288-27296, 2012.

\* cited by examiner

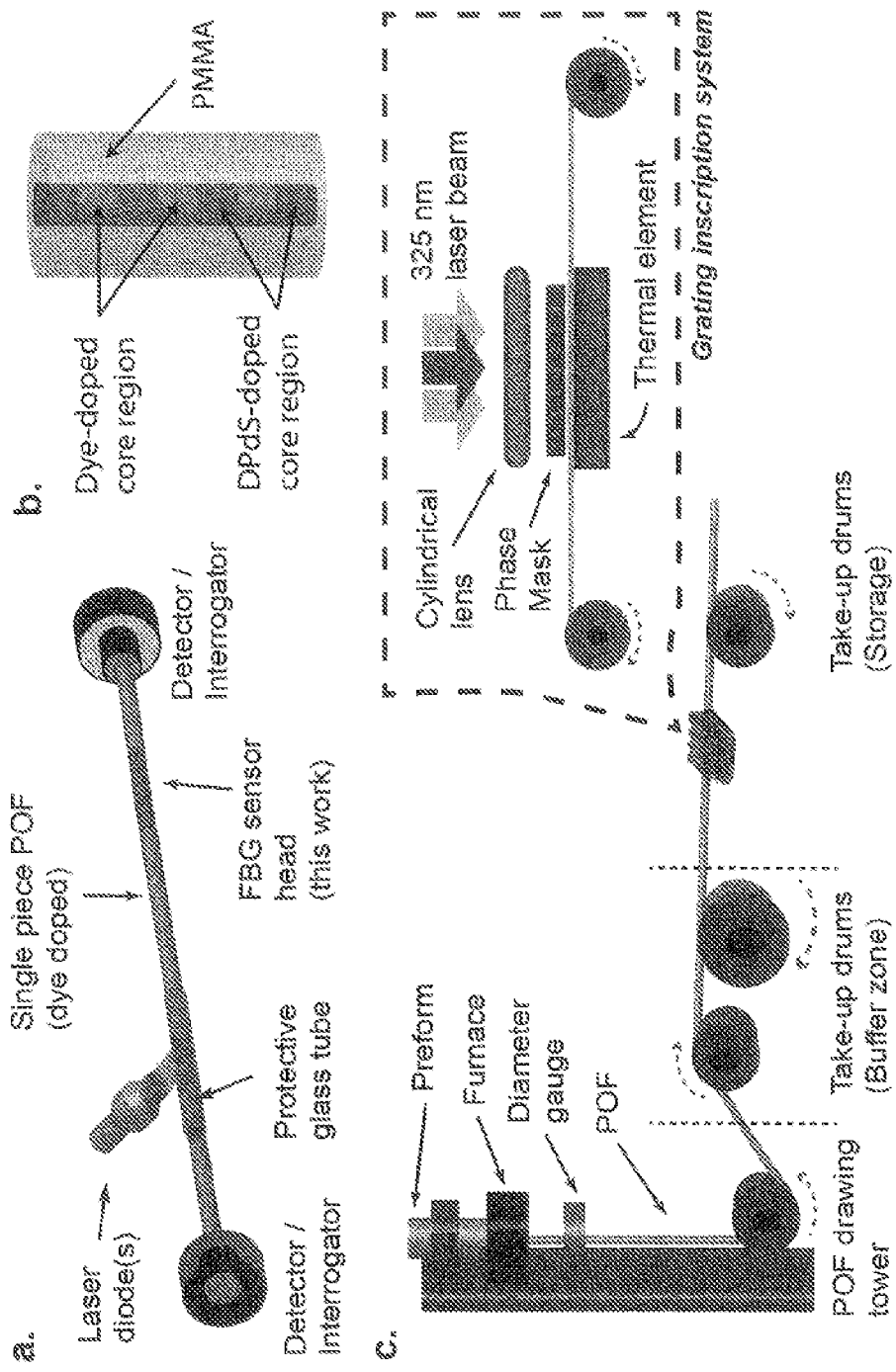
Figures 1(a)-(c)

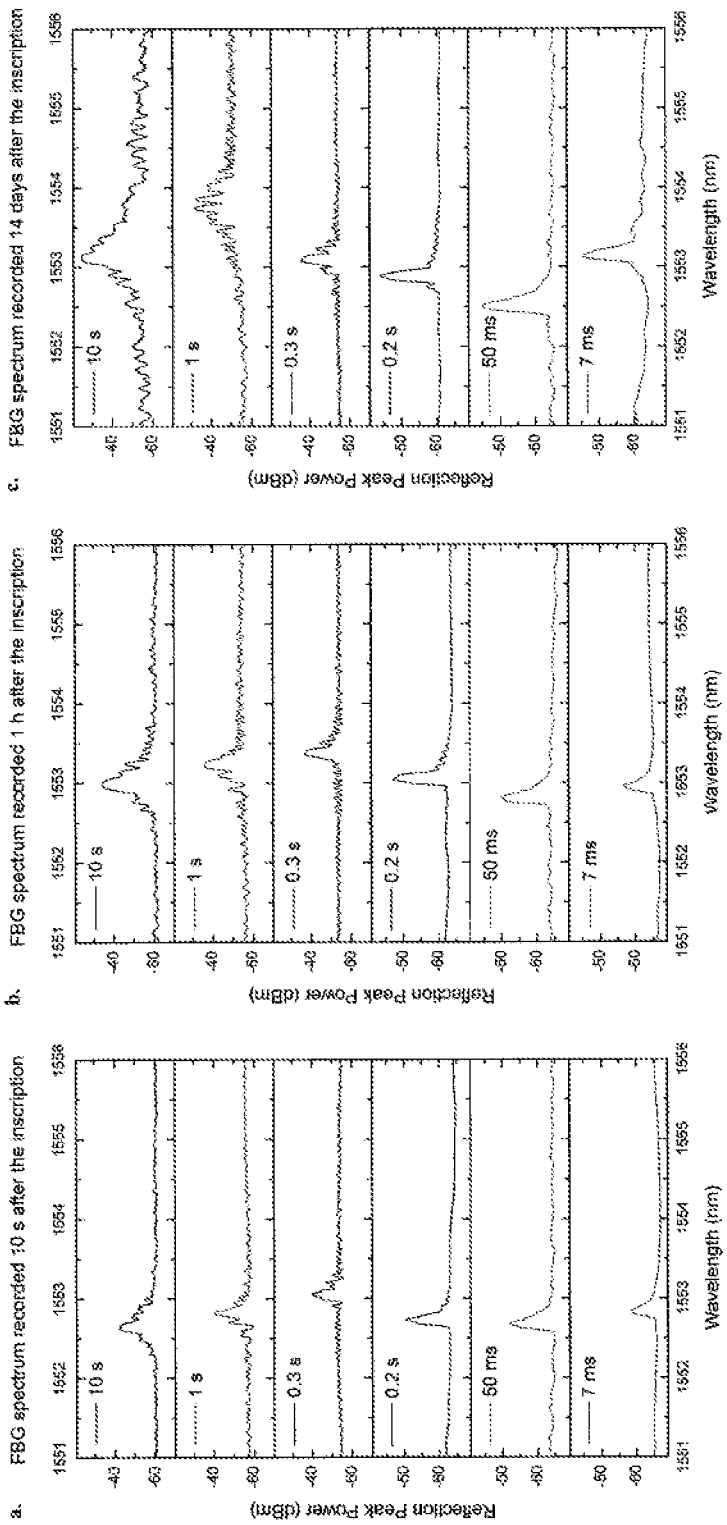
Figures 2(a)-(c)

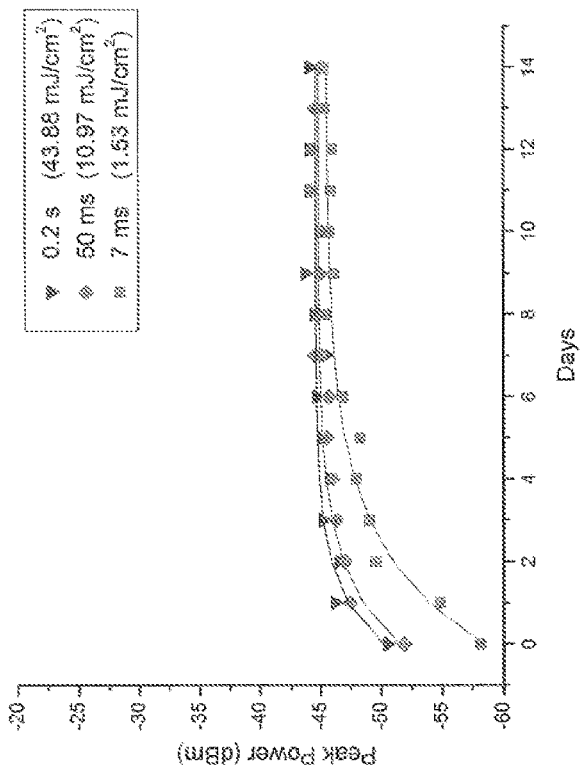
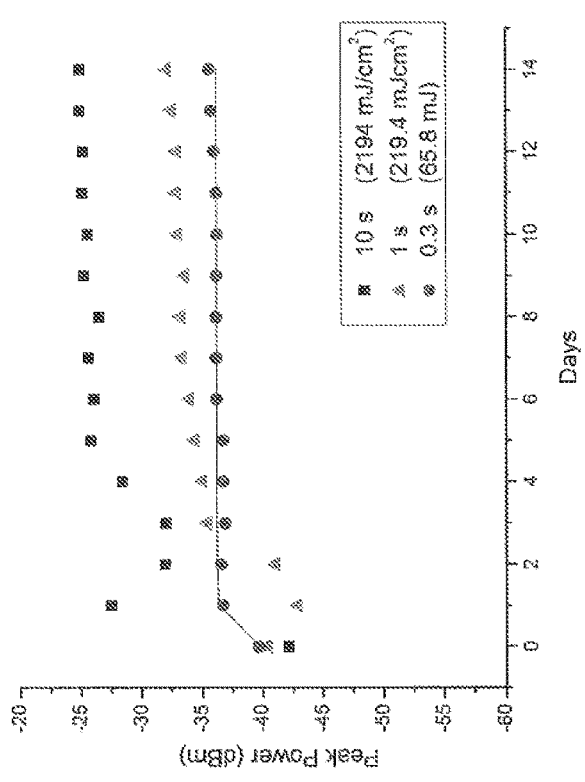
Figures 3(a)-(b)

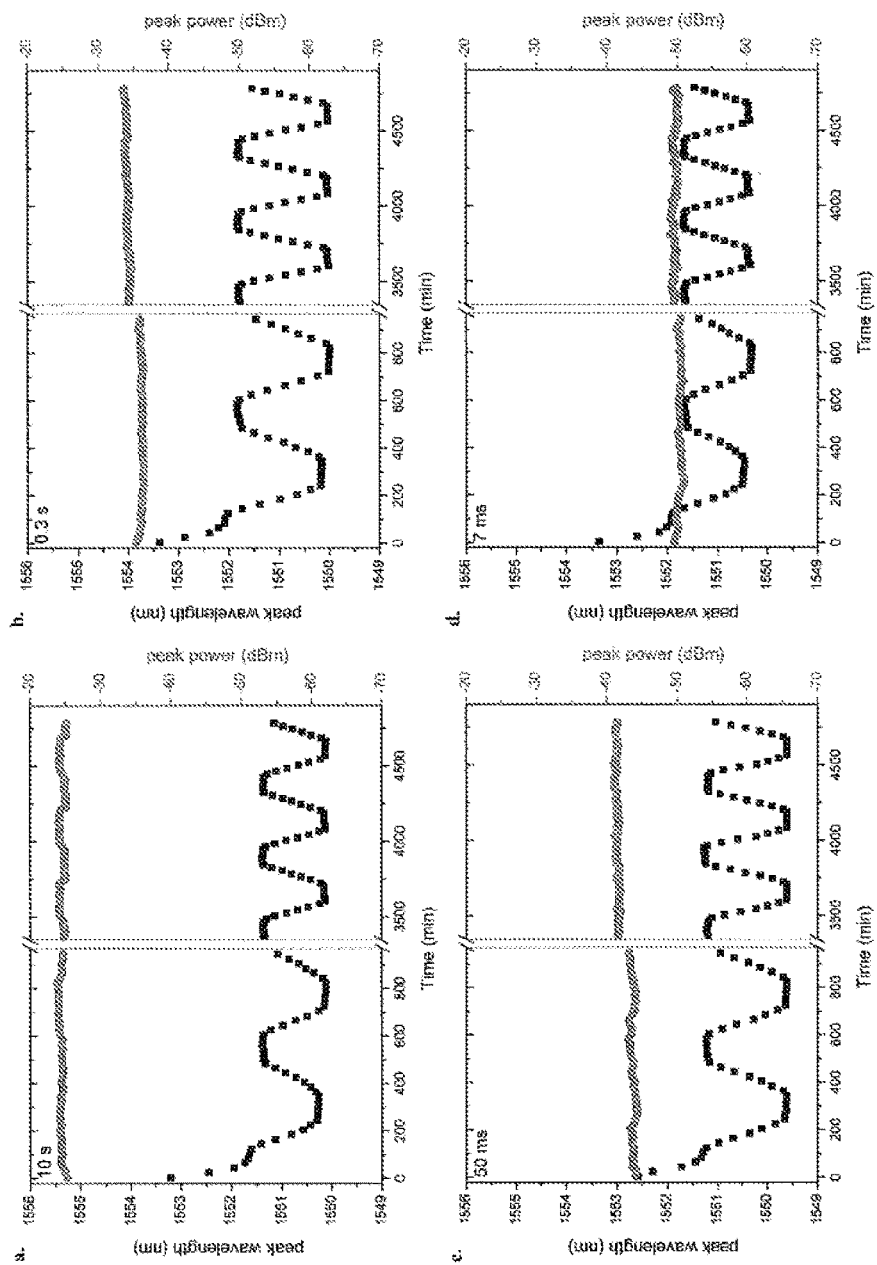
Figures 4(a)-(d)

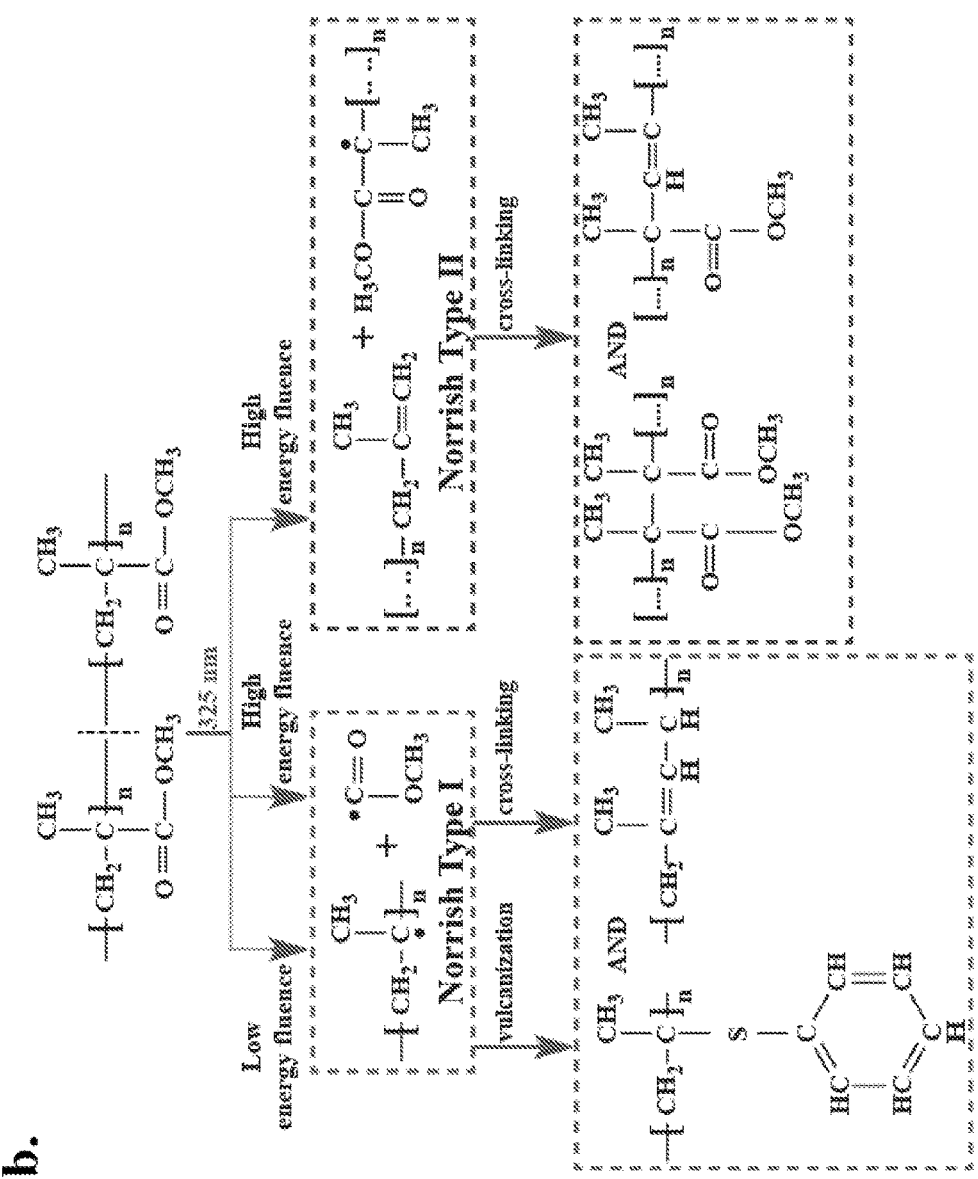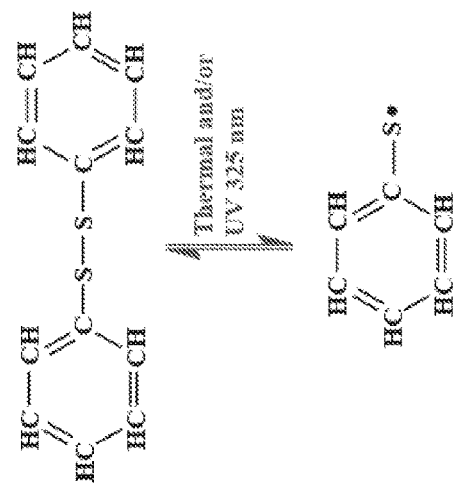
Figures 5(a)-(b)

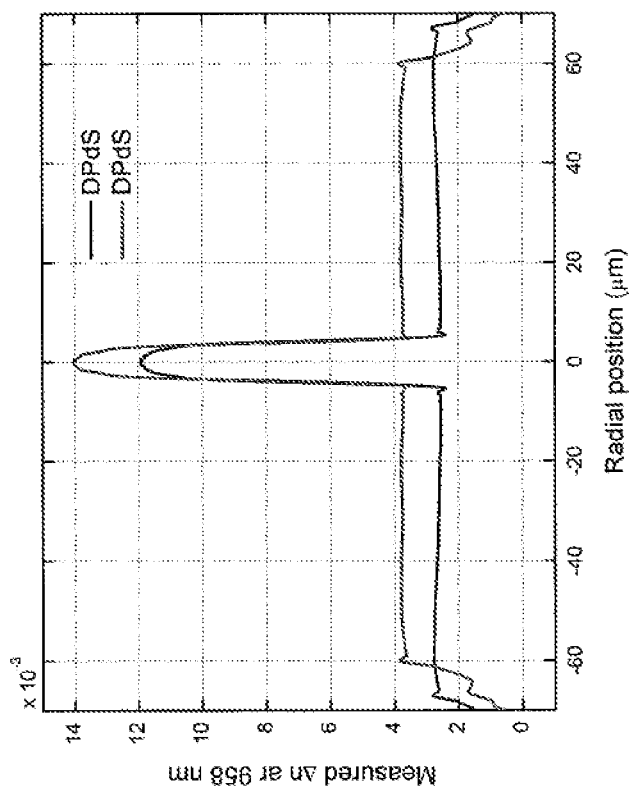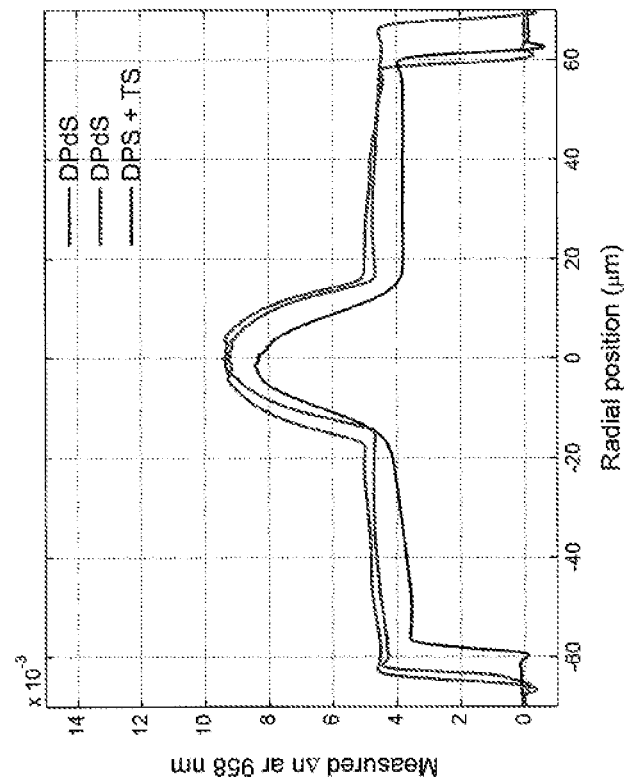
Figure 8

POLYMERIC WAVEGUIDE WITH SINGLE DOPANT

The present invention relates to the use of dopants for polymer optical fibres or polymer waveguides containing the dopants, sensors in the polymer optical fibres or polymer waveguides, which may be used in the biomedical industry for the measurement of different physiological and physical variables.

Fibre Bragg gratings (FBGs) inscribed inside the 8 or 9 μm core of single mode optical fibres are presently employed as optical fibre sensors in a large variety of applications. However, polymer optical fibres (POFs) are preferred for use in some applications, particularly in medical applications, because POFs offer many important advantages in comparison with glass fibres.

Specifically, POFs are biocompatible, immune from magnetic interference, incorporate biomaterials more easily, do not produce shards when they break, and are comparatively inexpensive to produce. FBGs inscribed in POFs could be used to measure variables such as strain, pressure, temperature, liquid flow rate, displacement, etc. Furthermore, POFs can be functionalised so that they can allow DNA sensing and drug delivery due to the low processing temperature of polymers that permit the incorporation of organic materials in POFs during the fabrication process. These are essential features for single-use in vivo medical applications.

However, existing POFs are not sufficiently photosensitive. This means that a long writing time, of up to 60 minutes or more, is typically required to inscribe an FBG; the fastest recorded inscription time using a 325 nm He—Cd laser of 7 minutes was reported in 2014 (Bundalo, I.-L., Nielsen, K., Markos, C. & Bang, O. Bragg grating writing in PMMA microstructure polymer optical fibres in less than 7 minutes. Opt. Express 22, 5270-5276 (2014)), and a faster grating inscription of 20 seconds was recently reported using a high peak-power 248 nm excimer laser (Oliveira, R. et al. Bragg gratings in a few mode micro structured polymer optical fibre in less than 30 seconds Opt. Exp. 23, 10181-10187 (2015)). However, even 20 seconds is still far too long to inscribe gratings during a fibre drawing process.

Previously, the photosensitivity and refractive index of the core of a POF have been increased by using two different materials, one material for each characteristic. For example, a dopant such as trans-4-stilbenemethanol (TS) was employed to impart enhanced photosensitivity, and benzyl methacrylate (BzMA) was employed to impart an increased refractive index for guiding of light in POFs. Later, BzMA was replaced by diphenyl sulfide (DPS) because of its lower transmission loss; though still two materials were required.

Furthermore, launching light into a POF to interrogate the FBG sensors is typically achieved by connecting the POF to the output glass fibre of a light source. This introduces two issues: (1) precise alignment of the 8 μm diameter core of glass fibre to a similar diameter core size of POF is needed in order to avoid a large optical loss; and (2) a fragile connection between the glass fibre and POF.

Furthermore, poly methyl methacrylate (PMMA), which is commonly used as the polymer backbone, starts to degrade upon UV irradiation below about 300 nm—such as that provided by an excimer laser.

Of course, in biomedical applications, the sensor head is preferably disposable and body-safe, and reliability and accurate measurement are very important factors. An ideal candidate is a sensor comprising a polymer fibre Bragg grating that can be fabricated rapidly (i.e. less than 1 second), preferably using UV irradiation that is beyond 300 nm to avoid degradation issues, mass-producible, and thus would lead to low production cost. However, such a product does not currently exist.

Furthermore, it would be desirable to be able to combine the light source and sensing elements in a single POF, thus eliminating the costly coupling of light from a source to the sensor head. This would provide a complete all-in-one technology platform for the realization of low-cost single-use biomedical sensors.

Therefore, in accordance with a first aspect of the present invention, there is provided a polymer optical waveguide comprising a single dopant material, wherein the single dopant material comprises:

at least two phenyl rings linked by a disulfide bridge; or
at least two phenyl rings linked by a sulfide bridge.

Advantageously, the single dopant materials used in the present invention increase the core refractive index and photosensitivity of a polymer optical waveguide to enable fibre Bragg gratings to be rapidly manufactured with a UV radiation exposure time of less than 1 second. Use of a single dopant material comprising at least two phenyl rings linked by a disulfide bridge; or at least two phenyl rings linked by a sulfide bridge reduces the attenuation of the polymer optical waveguide compared with waveguides doped with more than a single dopant material. Furthermore, a polymer optical waveguide according to the present invention possesses excellent thermal response.

The polymer optical waveguide may be a polymer optical fibre.

The polymer optical waveguide may be a polymer planar waveguide.

The polymer optical waveguide may be a single mode polymer optical fibre or a multimode polymer optical fibre.

The polymer optical waveguide may comprise alternating integrated light source sections and sensing sections. The integrated light source sections may be doped with laser dyes and the sensing sections may be doped with a single dopant material comprising:

at least two phenyl rings linked by a disulfide bridge; or
at least two phenyl rings linked by a sulfide bridge.

Advantageously, by integrating the light source into the photosensitive optical fibre, it is possible to manufacture a single mode optical fibre without the need for precise alignment of the light source to the photosensitive optical fibre which can lead to large optical loss. Furthermore, integrating the light source into the photosensitive optical fibre removes any need for a connection between a light source and a fibre which can be prone to breaking. Thus, a more robust single mode optical fibre which is less prone to optical loss can be manufactured by integrating the light source into the fibre itself. Whilst a preferred dopant material for the photosensitive optical fibre may comprise a single dopant material comprising at least two phenyl rings linked by a disulfide bridge; or at least two phenyl rings linked by a sulfide bridge, it will be apparent to a person skilled in the art that other suitable dopants may be used to achieve a single mode polymer optical fibre which is more robust and less susceptible to optical losses.

Also provided within the present invention is a sensor system comprising a polymer optical fibre that comprises a single dopant material, wherein the single dopant material comprises:

at least two phenyl rings linked by a disulfide bridge; or
at least two phenyl rings linked by a sulfide bridge.

Also provided within the present invention is a method of measuring one or more physical, physiological or biomedical variables comprising using a sensor system comprising a single dopant material, wherein the single dopant material comprises:
- at least two phenyl rings linked by a disulfide bridge; or
- at least two phenyl rings linked by a sulfide bridge.

Also provided within the present invention is a use of a sensor system in the measurement of one or more physical, physiological or biomedical variables, the sensor system comprising a single dopant material, wherein the single dopant material comprises:
- at least two phenyl rings linked by a disulfide bridge; or
- at least two phenyl rings linked by a sulfide bridge.

While it is known in the art to use a combination of dopant materials, such as TS and DPS as discussed above, to date it has never been possible to achieve rapid inscription of FBGs using only one single dopant material in the manufacture of POFs. Using the single dopant material in accordance with the invention, polymer preforms can be synthesized that can be drawn to ultra-photosensitivity POF without using BzMA or TS, which have demonstrated to improve the photosensitivity of POFs and shorten the FBG inscription time in BzMA or TS doped POFs from 10's of minutes to several minutes.

As the single dopant material, any chemical compound comprising two phenyl rings linked together by either a disulfide (—S—S—) bridge, or a sulfide bridge (—S—) is envisaged within the scope of the invention. One or more of the phenyl groups may be substituted with one or more functional groups. The term "substituted" as used herein, refers to all permissible substituents of the compounds, including acyclic and cyclic, branched and unbranched, carbocyclic and heterocyclic, aromatic and nonaromatic substituents. Illustrative substituents include, but are not limited to, halogens (F, Cl, Br, I), hydroxyl groups, or any other organic groupings containing any number of carbon atoms, preferably 1-14, and more preferably 1-10, or 1-6 carbon atoms (including methyl, ethyl, propyl, butyl, pentyl and hexyl), and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, nitro, amino, alkoxy, substituted alkoxy groups, or carboxylic acid groups (e.g. COOH). The functionalization may be located on any one or more of the positions on the phenyl ring(s), and different substituents may be substituted onto the same phenyl ring. If desired, one ring may be substituted while the other remains unsubstituted.

It is to be further understood that where descriptions of various embodiments use the term "comprising," those skilled in the art would understand that in some specific instances, an embodiment can be alternatively described using language "consisting essentially of or "consisting of."

Examples of compounds comprising phenyl rings linked by a disulfide bridge include, but are not limited to:
Diphenyl disulfide (also referred to as: Phenyl disulfide, NSC 2689)

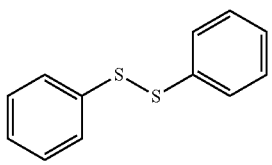 [SMILES: c1ccc(SSc2ccccc2)cc1]

Dibenzyl disulfide (also referred to as: DBDS, Benzyl disulfide, Bis(phenylmethyl) disulfide)

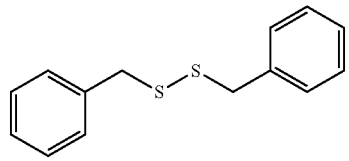 [SMILES: c1ccc(CSSCc2ccccc2)cc1]

3,3'-Dihydroxydiphenyl disulfide

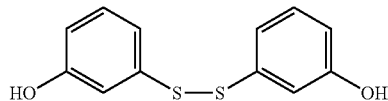 [SMILES: Oc1cccc(SSc2cccc(O)c2)c1]

4-Aminophenyl disulfide (also refer as: 4,4'-Dithiodianiline)

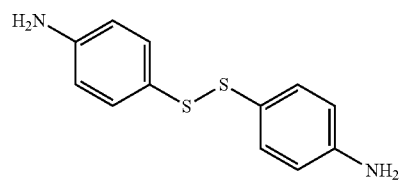 [SMILES: Nc1ccc(SSc2ccc(N)cc2)cc1]

2-Nitro-p-tolyl disulfide

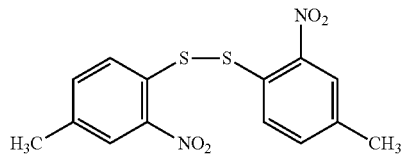

Thulium Ionophore I (also referred to as: 2,2'-Diaminodiphenyl disulfide, 2,2'-Dithiodianiline, Bis(2-aminophenyl) disulphide, 2-Aminophenyl disulphide)

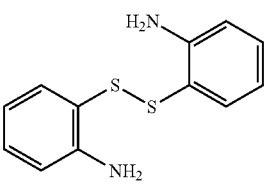 [SMILES: Nc1ccccc1SSc1ccccc1N]

Bis(4-methoxyphenyl) disulfide

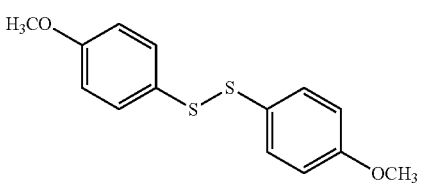 [SMILES: COc1ccc(SSc2ccc(OC)cc2)cc1]

4-Nitrophenyl disulfide (also referred to as: p,p'-Dinitrodiphenyl disulfide, Bis(4-nitrophenyl) disulfide, Bis(p-nitrophenyl) disulfide, NSC 4566, NSC 677446)

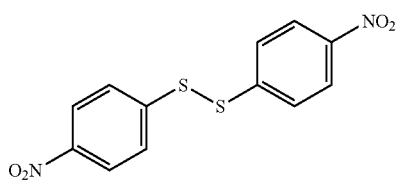 [SMILES: O=[N+]([O-])c1ccc(SSc2ccc([N+](=O)[O-])cc2)cc1]

Bis(4-chlorophenyl) disulfide (also referred to as: 4,4'-Dichlorodiphenyl disulphide)

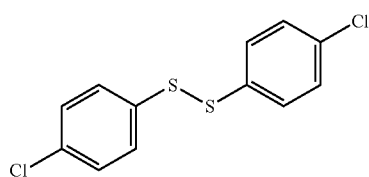 [SMILES: Clc1ccc(SSc2ccc(Cl)cc2)cc1]

2,2'-Dithiodibenzoic acid (also referred to as: 2-Carboxyphenyl disulfide, Bis(2-carboxyphenyl) disulfide, Dithiosalicylic acid)

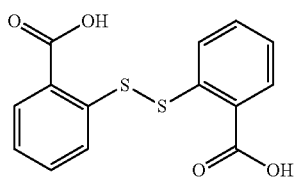 [SMILES: O=C(O)c1ccccc1SSc1ccccc1C(=O)O]

4-Bromophenyl Disulfide

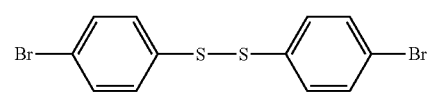 [SMILES: Brc1ccc(SSc2ccc(Br)cc2)cc1]

Bis(2-nitrophenyl) disulfide (also referred to as: 2-Nitrophenyl disulfide)

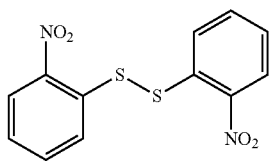 [SMILES: O=[N+]([O-])c1ccccc1SSc1ccccc1[N+](=O)[O-]]

Bis(thiobenzoyl) disulfide

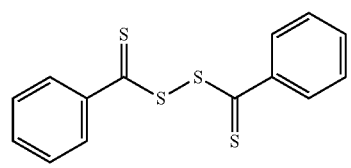 [SMILES: S=C(SSC(=S)c1ccccc1)c1ccccc1]

Bis(3,5-dichlorophenyl) disulfide

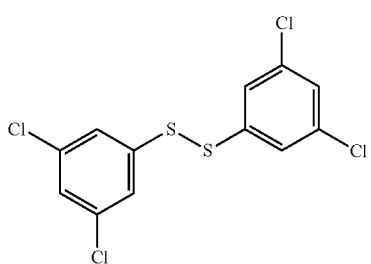 [SMILES: Clc1cc(Cl)cc(SSc2cc(Cl)cc(Cl)c2)c1]

1-CHLORO-2-((2-CHLOROPHENYL)DITHIO)BENZENE

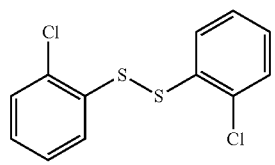 [SMILES: Clc1ccccc1SSc1ccccc1Cl]

p-Tolyl disulfide

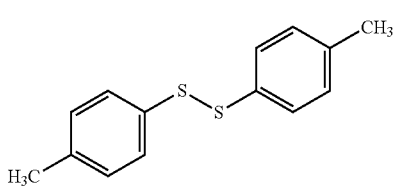

5,5'-Dithiobis(2-nitrobenzoic acid) also referred to as: 3-Carboxy-4-nitrophenyl disulfide, 6,6'-Dinitro-3,3'-dithiodibenzoic acid, Bis(3-carboxy-4-nitrophenyl) disulfide, DTNB, Ellman's Reagent

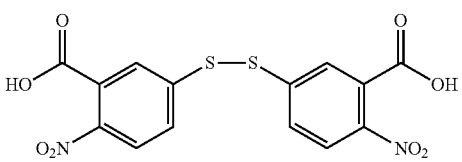 [SMILES: O=C(O)c1cc(SSc2ccc([N+](=O)[O-])c(C(=O)O)c2)ccc1[N+](=O)[O-]]

As used in the specification and the appended claims, the phrase "comprises at least two phenyl rings linked by a disulfide bridge" is intended to refer to any materials, substances and compounds comprising two substituted or unsubstituted, phenyl rings linked by a sulfur-sulfur (S—S) bond. This also includes compounds where the S—S linkage is not directly bonded to one or both of the phenyl groups.

Examples of compounds comprising a sulfur atom bridging two phenyl groups include, but are not limited to:

Diphenyl sulfide (DPS) (also referred to as: Phenyl sulfide)

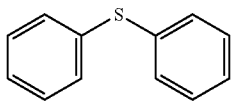 [SMILES: c1ccc(Sc2ccccc2)cc1]

Dibenzyl sulfide (also referred to as: Benzyl sulfide)

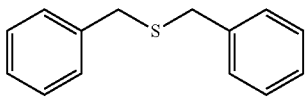 [SMILES: c1ccc(CSCc2ccccc2)cc1]

Diphenyl sulfoxide (also referred to as: Phenyl sulfoxide)

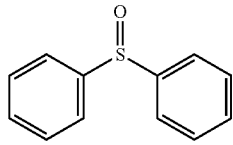 [SMILES: O=S(c1ccccc1)c1ccccc1]

Diphenyl sulfone (also referred to as: Phenyl sulfone)

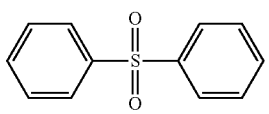 [SMILES: O=S(=O)(c1ccccc1)c1ccccc1]

p-Tolyl sulfoxide

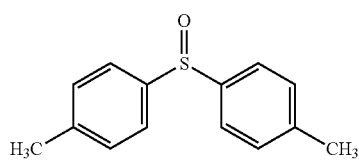

Di-p-tolyl sulfone

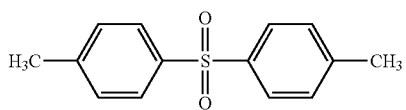

Thianthrene

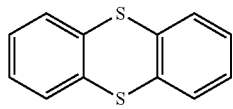 [SMILES: c1ccc2c(c1)Sc1ccccc1S2]

4,4'-Diaminodiphenyl sulfide (also referred to as: 4,4'-Thiodianiline)

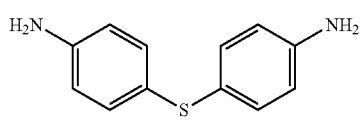 [SMILES: Nc1ccc(Sc2ccc(N)cc2)cc1]

2,2'-Diaminophenylsulfide (also referred to as: 2,2'-Thiodianiline)

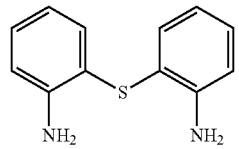 [SMILES: Nc1ccccc1Sc1ccccc1N]

2-(Phenylthio)aniline (also referred to as: 2-Aminophenyl phenyl sulphide)

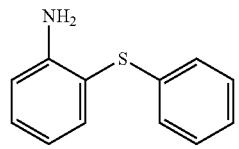 [SMILES: Nc1ccccc1Sc1ccccc1]

2-Nitrophenyl phenyl sulfide

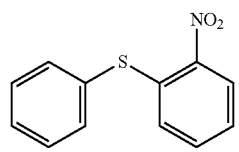 [SMILES: O=[N+]([O-])c1ccccc1Sc1ccccc1]

2-Nitrophenyl phenyl sulfone

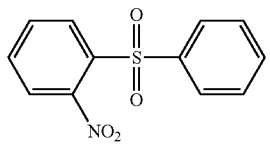

4,4'-Thiodiphenol (also referred to as: 4-Hydroxyphenyl sulfide, TDP)

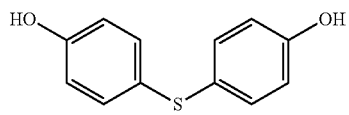 [SMILES: Oc1ccc(Sc2ccc(O)cc2)cc1]

Bis[4-(2-hydroxyethoxy)phenyl]sulfone

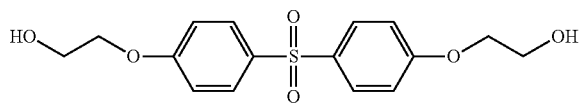 [SMILES: O=S(=O)(c1ccc(OCCO)cc1)c1ccc(OCCO)cc1]

4,4'-Sulfonylbis(2-methylphenol)

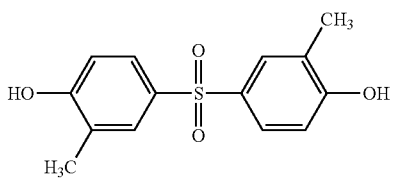 [SMILES: Cc1cc(S(=O)(=O)c2ccc(O)c(C)c2)ccc1O]

Bisphenol S (also referred to as: 4,4'-Sulfonyldiphenol, 4-Hydroxyphenyl sulfone, Bis(4-hydroxyphenyl) sulfone)

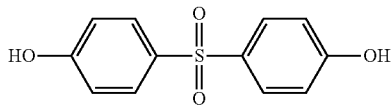 [SMILES: O=S(=O)(c1ccc(O)cc1)c1ccc(O)cc1]

Bis(4-chlorophenyl) sulfone (also referred to as: 4,4'-Dichlorodiphenyl sulfone)

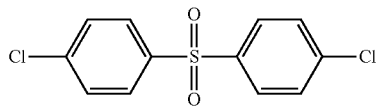 [SMILES: O=S(=O)(c1ccc(Cl)cc1)c1ccc(Cl)cc1]

4,4'-Thiobisbenzenethiol

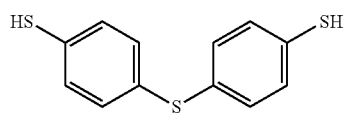 [SMILES: Sc1ccc(Sc2ccc(S)cc2)cc1]

2-(Phenylsulfonyl)aniline (also referred to as: 2-Aminophenyl phenyl sulfone)

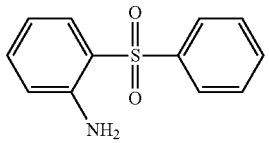

4-(Phenylthio)Aniline

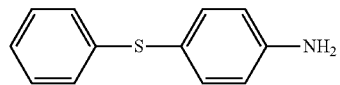 [SMILES: Nc1ccc(Sc2ccccc2)cc1]

4-Amino-4'-nitrodiphenyl sulfide (also referred to as: 4-(4-Nitrophenylthio)aniline)

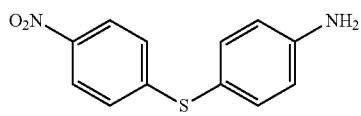 [SMILES: Nc1ccc(Sc2ccc([N+](=O)[O-])cc2)cc1]

4-Chloro-2-(phenylthio)aniline hydrochloride hydrate (also referred to as: 4-Chloro-2-(phenylsulfanyl)aniline hydrochloride hydrate)

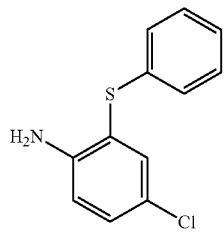 [SMILES: Nc1ccc(Cl)cc1Sc1ccccc1]

For illustrative purposes, DPdS or DPS is employed as the single dopant material. It is well known to a person skilled in the art that compounds with a disulfide bridge are easily cleaved under UV, thereby generating a radical in the form R—S.

As used in the specification and the appended claims, the phrase "comprises at least two phenyl rings linked by a sulfide bridge" is intended to refer to any materials, substances and compounds comprising two optionally substituted or unsubstituted, phenyl rings linked by at least one bridge containing at least one sulfur atom, e.g. a carbon-sulfur (C—S) bond. These materials, substances and compounds are understood by a person of ordinary skill in the art as including compounds having a sulfide (—S—), sulfone (—SO2-) or sulfoxide (—SO—) linkage. As used herein, compounds containing more than one sulphide bridge may be used, such as thianthrene, depicted above.

For purposes of convenience only, we shall refer herein to the single dopant material comprising two phenyl rings. However, this is not indicative of the scope of the invention being limited thereto.

Each of these compounds, when used as the single dopant material, is able to achieve the desired effect of an increase in the core refractive index and photosensitivity. Typically, between about 0.1 to about 10, preferably about 2 to 8 mol %, and more preferably about 2 to 6 mol % of the single dopant material is employed.

The mechanism that leads to photosensitivity in PMMA optical fibres under UV irradiation is rather complicated. Historically, 325 nm is the wavelength used for majority of the work on FBG inscription in POFs, because PMMA starts to degrade upon UV irradiation below about 300 nm and 325 nm is one of the main emission lines of a HeCd laser.

Prior to UV irradiation, each diphenyl disulphide molecule in the fibre core is composed of two phenyl groups linked together through a single bond between 2 sulphur atoms, and is not attached to the PMMA backbone. The S—S bond of diphenyl disulphide can be broken by either heat or under UV irradiation. Under UV irradiation, homolysis of the diphenyl disulphide occurs and two sulphenyl radicals are created. This is shown in FIG. 5a.

Concurrently, the PMMA undergoes different transformations, depending on UV energy fluences. Side chain scission (a Norrish type I photochemical reaction) occurred when irradiated with low UV energy fluence. However, under strong UV energy fluence, both side chain scission and main chain scission (Norrish type II photochemical reaction) occur. This is shown in FIG. 5b. The energy needed to break the disulphide bond in DPdS is very low (214.2 kJ/mol) in comparison with other core dopants, such as diphenyl sulphide (327.6 kJ/mol). The sulphenyl radicals are then anchored to the PMMA main chain through the sulphur atoms via a chemical process called vulcanization, and the induced refractive index of the fibre core increases, which explains the fast induced-photosensitivity of the POFs of the invention. Good quality FBGs were inscribed in the DPdS-doped POFs with UV irradiation using a 325 nm He—Cd laser, and in a time of only 7 ms. This inscription time is more than 4 orders of magnitude faster than previously reported Bragg gratings inscribed with 325 nm laser in polymer optical fibres of any kind.

In the case of the disulphide bridge in compounds such as DPdS, cleavage of the S—S bond occurs upon UV irradiation, creating two PhS. radicals.

The bond dissociation energy of the C—S bond is higher than that of an S—S bond, which means that a longer irradiation time is necessary to fabricate FBGs using DPS than using DPdS. However, the principle of refractive index modulation under UV irradiation is the same for DPS as for DPdS. The PhS. radical created by the UV-induced cleavage of the C—S bond of DPS will also anchor to the PMMA backbone of the POF and alter the refractive index and photosensitivity.

As discussed above, the present invention provides a 3-dimensional POF design that integrates POF light sources with photosensitive POFs, and a new POF doped with a single dopant material as defined hereinabove, which increases the refractive index and introduces a greater photosensitivity in the fibre core, thus enabling an FBG inscription time of only milliseconds. This permits the fabrication of a polymeric sensing platform during a polymer optical fibre drawing process, integrating light source and Bragg grating sensors in the same fibre during the process, leading to lower manufacturing costs for single-use in vivo medical sensors.

The 3-D polymer optical fibre design also permits a single optical fibre with a section of the fibre serving as light source to interrogate adjacent sections of the same fibre with inscribed FBG sensors. It solves the light coupling issue from glass optical fibre to POFs and also eliminates the fragile connection between a glass fibre and a POF.

It is also possible to precisely control and optimize the refractive index profile of the fibre to make a high-quality single mode polymer optical fibre with a large core diameter, for ease of light coupling. This is achieved by using different dopant concentrations and optimising the geometrical design of the fibre. Control of the fibre core diameter is possible because of the novel "pull through" technique that virtually eliminates dopant diffusion from fibre core to cladding.

In the manufacture of POFs, any suitable polymer can be used that would be apparent to a person skilled in the art. However, PMMA is the preferred material to produce POFs, due to its high optical transparency and because it possesses a similar refractive index to that of conventional silica telecommunication optical fibre.

Other suitable polymer materials include:
perfluorinated polymers obtained by copolymerization of 2,2-bis(trifluoromethyl)-4,5-difluoro-1,3-dioxole and tetrafluoroethylene (TFE), copolymerization of perfluoro-2,2,4-trifluoro-5-trifluoromethoxy-1,3-dioxole and tetrafluoroethylene (TFE), and homopolymerization of perfluoro(1-butenyl vinyl ether) (PFBVE);
deuterated PMMA based fibres: perdeuterated PMMA (PMMA-$d_8$) which exhibits lower attenuation but very high water sorption;
partially halogenated polymers: POF with core base materials: poly(2,2,2-trifluoroethyl methacrylate) (poly(T-FEMA), poly(2,2,2-trichloroethyl methacrylate) (poly(TCIEMA)), and MMA-co-pentafluorophenyl methacrylate (PFPhMA);
polystyrene derivatives: poly(2,3,4,5,6-pentafluorostyrene), poly(2-trifluoromethyl styrene);
perfluorinated polydioxolane derivatives: perfluoro-2-methylene-4-methyl-1,3-dioxolane, perfluoro-2-methylene-4,5-dimethyl-1,3-dioxolane, poly(perfluoro-2-methylene-1,3-dioxolanes); and
copolymers of perfluoromethylene dioxalanes and fluorovinyl monomers: Copolimerization of perfluoro-3-methylene-2,4-dioxabicyclo[3.3.0]octane with chlorotri-fluoroethylene (CTFE), perfluoropropyl vinyl ether, perfluoromethyl vinyl ether, and vinylidene fluoride.

Once the FBGs have been inscribed during the fibre drawing process, the fibres may subsequently be coated with functional polymers, such as a high chemical resistance material or a humidity resistance material, depending upon the specific intended application. Suitable coating materials include:
perfluorinated polymers obtained by copolymerization of 2,2-bis(trifluoromethyl)-4,5-difluoro-1,3-dioxole and tetrafluoroethylene (TFE), copolymerization of perfluoro-2,2,4-trifluoro-5-trifluoromethoxy-1,3-dioxole and tetrafluoroethylene (TFE), and homopolymerization of perfluoro(1-butenyl vinyl ether) (PFBVE);
partially halogenated polymers: POF with core base materials: poly(2,2,2-trifluoroethyl methacrylate) (poly(T-FEMA), poly(2,2,2-trichloroethyl methacrylate) (poly(TCIEMA)), and MMA-co-pentafluorophenyl methacrylate (PFPhMA);
polystyrene derivatives: poly(2,3,4,5,6-pentafluorostyrene), poly(2-trifluoromethyl styrene);
perfluorinated polydioxolane derivatives: perfluoro-2-methylene-4-methyl-1,3-dioxolane, perfluoro-2-methylene-4,5-dimethyl-1,3-dioxolane, poly(perfluoro-2-methylene-1,3-dioxolanes); and
copolymers of perfluoromethylene dioxalanes and fluorovinyl monomers: Copolimerization of perfluoro-3-methylene-2,4-dioxabicyclo[3.3.0]octane with chlorotri-fluoroethylene (CTFE), perfluoropropyl vinyl ether, perfluoromethyl vinyl ether, and vinylidene fluoride.

The sensor containing the POF of the invention is typically manufactured using a fibre drawing process. This process involves a step where the POF preform is made by pulling a polymer optical fibre/rod which is doped with a photosensitive material such as DPdS, through a hole in the centre of a pre-made polymer preform cladding. This is done in order to eliminate dopant diffusion from the core into cladding, permitting the fabrication of step-change refractive index necessary for making good quality single-mode polymer optical fibres, which is essential for the fabrication of fibre Bragg grating sensors. Thereafter, the FBG is inscribed, typically by UV radiation.

Also provided in accordance with the invention is a method of manufacturing a polymer optical waveguide as defined hereinabove, comprising the steps of:
a) doping a polymer optical fibre with a single dopant material, wherein the single dopant material comprises: at least two phenyl rings linked by a disulfide bridge; or at least two phenyl rings linked by a sulfide bridge;

The method may further comprise the steps of:
b) inserting the doped polymer optical fibre though an opening in a pre-made polymer preform cladding to form a preform;
c) drawing the preform into a photosensitive polymer optical fibre; and
d) exposing the photosensitive polymer optical fibre to UV radiation to fabricate a fibre Bragg grating.

The polymer optical fibre may be a single mode polymer optical fibre.

The fibre Bragg grating (FBG) inscribed in POFs may be used for in vitro or in vivo measurements, or incorporated in wearable medical sensors which are used to monitor human vital signs. Further, FBGs weaved into fabrics could be used to measure variables such as pulse-rate, blood pressure as demonstrated by Y. Katsuragawa et H. Ishizawa (Y. Katsuragawa et H. Ishizawa. Non-invasive blood pressure measurement by pulse wave analysis using FBG sensor. 2015 IEEE International Instrumentation and Measurement Technology Conference (I2MTC) Proceedings, 511-515, (2015)), etc. The sensor may include additional components, such as means for generating light, photodetector, data storage system, display screen. etc.

The invention also allows for a simpler and more rapid fabrication of polymer planer waveguide devices such as waveguide grating filters, waveguide couplers, and waveguide combiners. Also envisaged within the present invention is the use of DPS or DPdS in rapid waveguide fabrication of planar photonic devices—which permit the writing of photonic devices directly on thin-layer of DPS or DPdS films without any chemical post-processing.

Most polymer waveguides are fabricated in an SU-8 photoresist using selective polymerization. This process involves many steps: spin-coated SU-8 layer of a few tens of µm thick, exposure to UV irradiation, a post-bake step, rinsing with isopropyl alcohol, drying with nitrogen, flood exposure, and hard-baking. In contrast, the fabrication of waveguide using a DPS or DPdS material would involve fewer steps: a spin-coated film followed by a polymerization, and then a patterning step with a UV laser beam.

The invention will now be described further by way of example with reference to the following examples which are intended to be illustrative only and in no way limiting upon the scope of the invention.

FIG. 1a shows a complete sensor system in which a section of the POF is doped with laser dye and side pumped by one or more low-cost laser diodes;

FIG. 1b shows a 3-D optical preform;

FIG. 1c shows production of drawing 3-D polymer fibre that integrates light sources and grating sensors during the fibre drawing process;

FIGS. 2a-2c show reflection spectra recorded after FSGs were inscribed at with different irradiation times in a POF, with gratings recorded 10 s after inscription (FIG. 2a), 1 hour after inscription (FIG. 2b); and 2 weeks after inscription (FIG. 2c);

FIG. 3a shows the growth of FBGs written in 10 s, 1 s and 0.3 s, over a period of two weeks;

FIG. 3b shows the growth of FBGs written in 0.2 s, 50 ms and 7 ms, over a period of two weeks;

FIGS. 4a-4d show the fluctuations in wavelength and peak power during temperature cycling. Temperature profiles set from 20 to 50° C. with steps of 2 h and 10 cycles are presented for (a) a 10 s FBG, (b) a 0.2 s FBG, (c) a 50 ms FBG and (d) a 7 ms FBG. Only the first 2 and last 3 cycles were plotted in the figure with the dash line representing the missing cycles;

FIGS. 5a and 5b show the fibre chemical constituents and chemical degradation of (a) Diphenyl Disulfide and its UV-induced cleavage, and (b) the PMMA repeating unit and UV-induced degradation.

Figure 6:
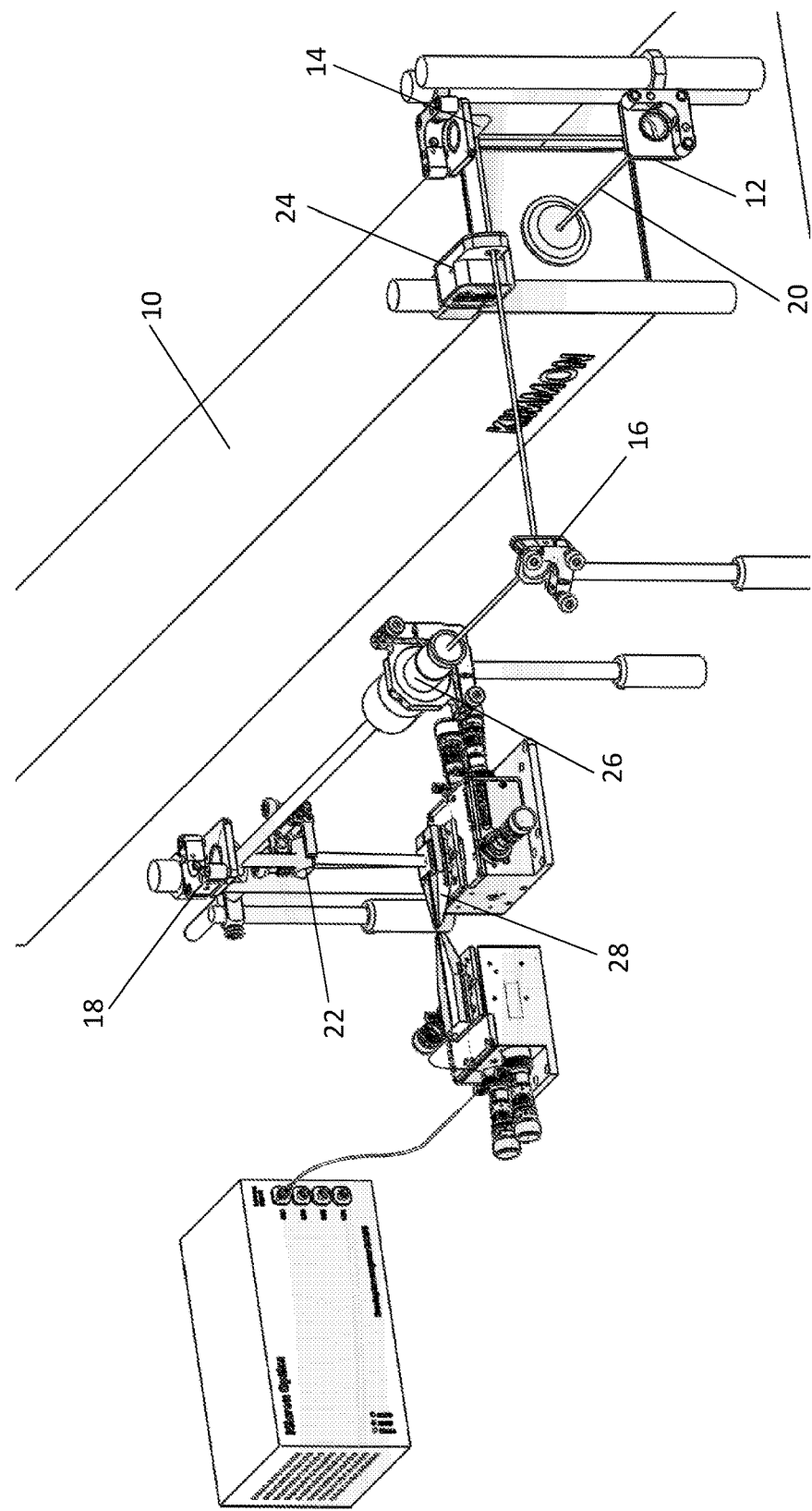

FIG. 6 shows a polymer optical FBG fabrication set up using a static beam.

Figure 7:
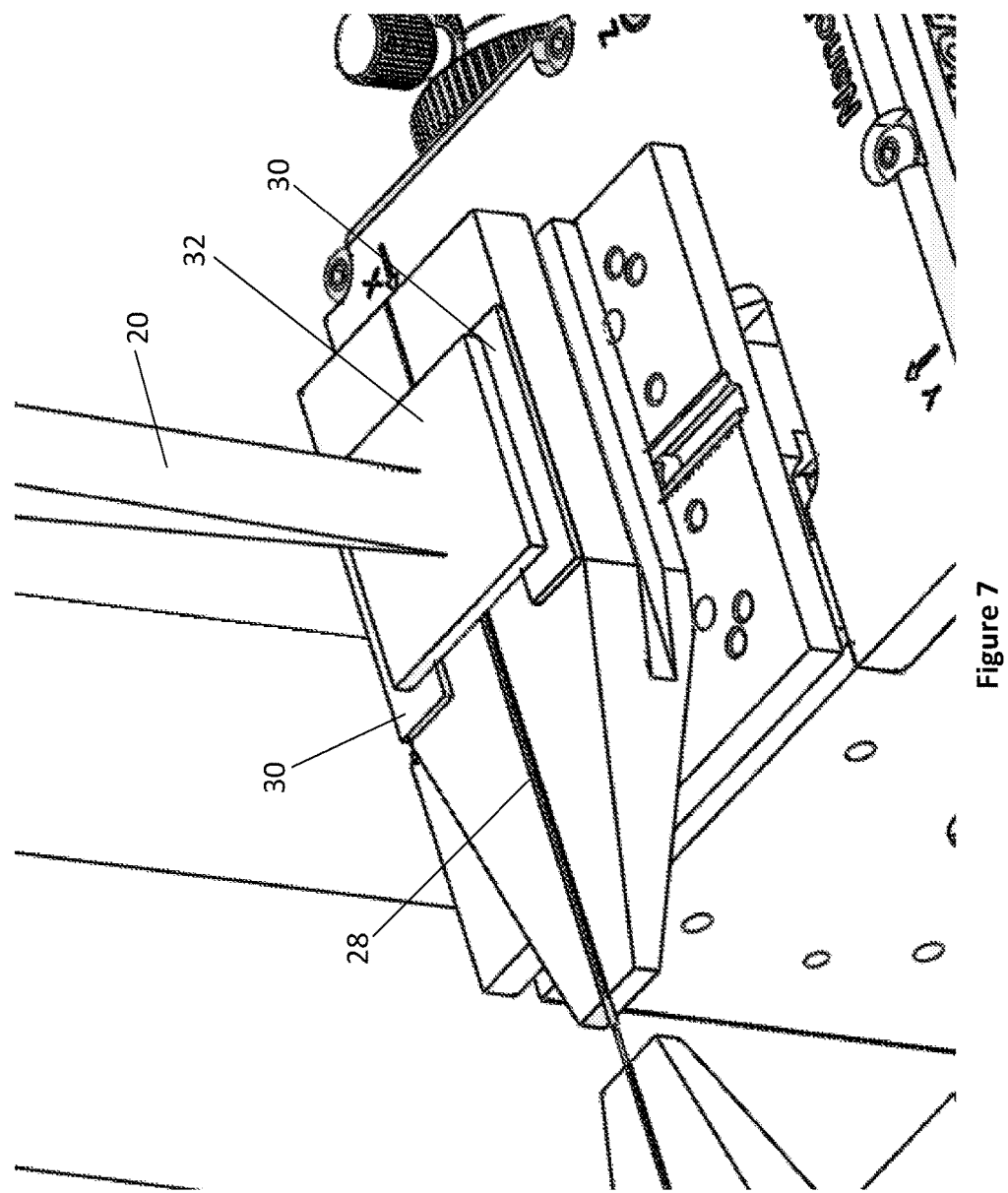

FIG. 7 shows a POF being secured into a V-groove for FBG fabrication.

FIG. 8 shows two graphs depicting the measured refractive index profiles of several samples of DPdS core doped POFs and DPS+TS core doped fibre fabricated using the Teflon string method (the left-hand graph) and DPdS core doped fibres fabricated using the pull-through method (the right-hand graph).

Figure 9:
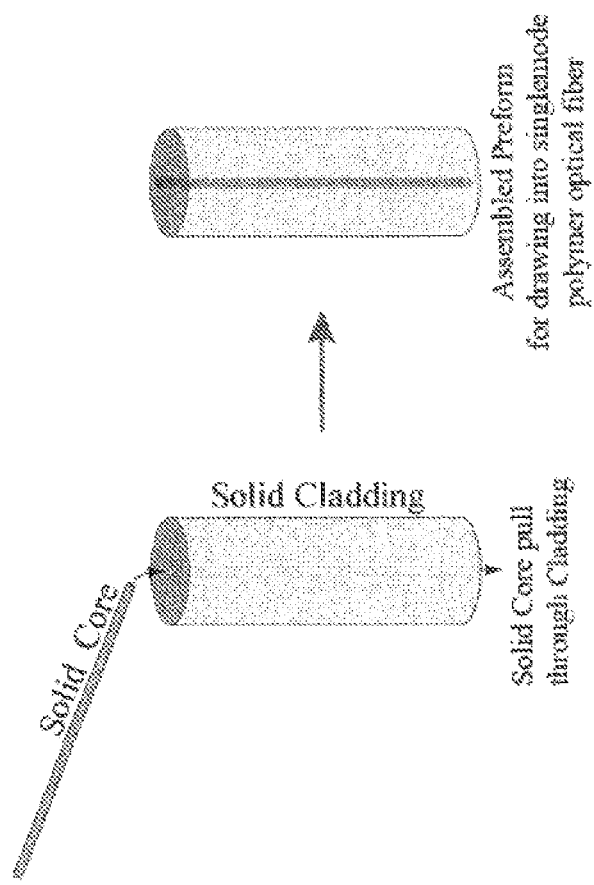

FIG. 9 shows the pulling of the solid core through the cladding to form the preform.

Figure 10:
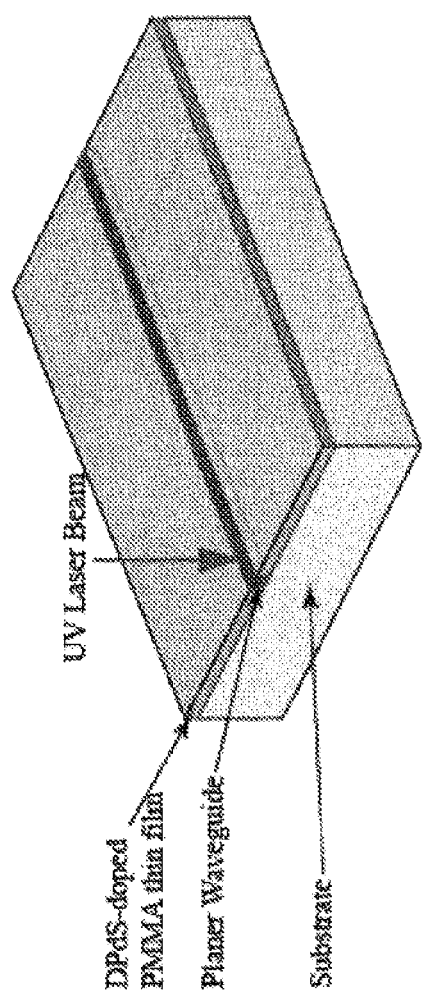

FIG. 10 shows a DPdS-doped PMMA thin film being used in the fabrication of a planar photonic device.

FIG. 1a depicts the complete sensor system in which a section of the POF is doped with laser dye and side pumped by one or more low-cost laser diodes. The pumping technique overcomes the problem of photo-bleaching by extending the lifetime of the fluorescence output of dye-doped POFs. The sensing section of the POF should be highly photosensitive, allowing fibre gratings to be inscribed in it rapidly.

The 3-D optical preform shown in FIG. 1b could be fabricated with high-resolution 3-D printers. The centre of the preform that eventually forms the core of the POF consists of alternative sections of laser-dye doped materials separated by photosensitive materials for rapid inscription of grating sensors. The production of the 3-D POF would require a high-resolution 3-D printer for the cladding material, the laser-dye doped material, and the photosensitive material.

FIG. 1c shows the production of drawing a 3-D polymer fibre that integrates light sources and grating sensors during the fibre drawing process. The major obstacle of this novel approach is to develop a highly photosensitive polymer that allows rapid grating inscription times of less than 1 second.

Here, with this short inscription time, gratings can be produced during the fibre-drawing process. A potential mass production scheme for the gratings is depicted in FIG. 1c. The whole drawing-and-writing process can be automated by synchronising the winding speed of the take-up mechanism. Production of gratings with different Bragg wavelengths in one production line is also possible by applying tension or applying simple thermal treatment to the POF section where the FBG is to be inscribed (see the inset of FIG. 1). This is because of the large thermal expansion and heat transfer coefficients of POFs.

EXAMPLES

Method
Polymer Optical Fibre Fabrication

All the fibre and associated results presented herein are drawn from preforms fabricated using the "pulled through" method whereby the core fibre/rod (doped with a photosensitive material such as DPdS), is pulled through a hole in the centre of a pre-made polymer preform cladding. This method, although similar, has not to be mistaken with the Teflon string method, where the core monomer is poured in the cladding preform. Such method was responsible of a large diffusion of the core material during polymerization.

Two steps were employed to fabricate the polymer preform, namely a pre-polymerization stage and a polymerization stage. The pre-polymerization process takes place in a glove box while the polymerization process is made in an oven. Firstly, the suitable weight of chemicals should be prepared using an electronic balance with optimal ratio between monomer (MMA), initiator and chain transfer to prepare the cladding preform. Secondly, all the chemicals were mixed and placed in a glove box filled with argon gas at a relatively constant pressure, until the cleaning standard reached the ISO 5 (particles of 0.5 um<3250 in the ISO 14644-1 cleanroom) standard. Afterwards, the solution was stirred and heated in an oil bath inside an argon atmosphere, to avoid any explosive polymerization occurring.

A particle counter was used to record particles with sizes of 0.3, 0.5, 1, 2 and 5 µm, and the temperature and humidity was recorded with a commercial detector. This process has allowed the inventors to fabricate preforms with lower dust particles and humidity, giving the fibres better properties than those made with a conventional process. After the pre-polymerization, the low viscosity solution was poured into a test tube in which a Teflon string has been fixed along the central axis. The Teflon string was pulled out of the preform, leaving the cladding part with a hole along the centre. The core mixture was prepared separately and poured into a glass tube. After curing in the oven, the core preform was drawn using a POF drawing tower into a rod. The rod was pulled through the central hole of the cladding preform. The assembled preform was then drawn into fibre. The final fibre diameter was 120 µm with 3% tolerance. This pulling of the rod, i.e. solid core through the cladding to form the preform is illustrated in FIG. 9.

Fibre Bragg Grating Inscription

With reference to FIGS. 6 and 7, a KIMMON He—Cd 325 nm laser 10 was used to fabricate the FBGs. Four mirrors 12, 14, 16, 18 were employed to guide the laser beam 20 from the laser to the POF, allowing the beam to reach a 150 mm plano-convex lens 22 placed right after the last mirror 18 to focus the beam 20 on the fibre. A beam shutter 24 was inserted in the optical path after the second mirror 14 and a 10× beam expander 26 was placed after the third mirror 16 to expand the beam 20 from 1.2 to 12 mm.

The fibre was secured into a Newport 125 µm V-groove 28 using tape 30 and 2 layers of regular tape were placed on each side of the V-groove 28, on which was placed the Ibsen phase mask 32 for FBG fabrication. The phase mask pitch was 1046.3 nm. The tape thickness was around 60 µm per layer, allowing a short distance between the fibre and the phase mask 32 without damaging it. In FIG. 8, one can see the measured refractive index profiles of several samples of DPdS core doped POFs and DPS+TS core doped fibre fabricated using the Teflon string method (the left-hand graph) and DPdS core doped fibres fabricated using the pull through method (the right-hand graph).

The POFs used were 120 µm thick, and the core diameter was 5.5 µm, consisting of 96 mol % PMMA and 4 mol % DPdS. The Reflection spectrum was investigated using a SMF-28 fibre with the end cut with an angle of 8 degrees (to annihilate the Fresnel reflection) and a Micron Optics SM 125 interrogator which range from 1510 nm to 1590 nm and resolution of 5 pm. All the FBGs were 10 mm long. FBGs of much shorter length (<1 mm) were also successfully inscribed in the POF in less than 1 second.

The refractive-index profiles of samples of POFs, fabricated with two different methods, were measured using a fibre index profiler (IFA100™ from Interfibre Analysis), with the refractive index measurements compared between two DPdS core doped POF and one DPS+TS core doped fibre fabricated using the Teflon string method.

In the case of the DPS+TS core doped fibre, serious dopants diffusion from core to cladding can be observed which occurred during the core polymerization process, making it difficult to produce single-mode fibre. In the case of the DPdS core doped POF, virtually no dopant diffusion was observed. This results in an observed excellent abrupt change in the refractive index between the core and cladding.

The averaged transmission loss of the DPdS POF was measured by the multiple cutback method and the fibres were cut by hand using a hot plate and razor blade. Attenuation measurements were carried out at 870 nm and 1550 nm.

Tables 1 and 2 show attenuation data comparing for multimodes fibres comprising different dopant materials: DPS+TS, DPS alone, or DPdS alone, using a wavelength of 870 nm and 1550 nm, respectively.

TABLE 1

| Core Dopant | Attenuation (dB/m) |
| --- | --- |
| DPS + TS | 39.27 |
| DPS | 24.12 |
| DPdS | 18.17 |

TABLE 2

| Core Dopant | Attenuation (dB/m) |
| --- | --- |
| DPS + TS | 135.66 |
| DPS | 91.74 |
| DPdS | 96.16 |

It can be seen that for multimode fibres operating at a wavelength of 870 nm and 1550 nm respectively, the attenuation reduces significantly. The reduction is by as much as 39% at 870 nm and 32% at 1550 nm, when using DPS alone as the dopant material, in comparison with DPS+TS. This improvement is even more marked at 870 nm when DPdS is used as the sole dopant material, with a reduction in attenuation of 52% being observed. A reduction in attenuation of 29% at 1550 nm can also be achieved when DPdS is used as the sole dopant material.

Tables 3 and 4 show attenuation data comparing for single mode fibres comprising different dopant materials: DPS+TS, DPS alone, or DPdS alone, using a wavelength of 870 nm and 1550 nm, respectively.

TABLE 3

| Core Dopant | Attenuation (dB/m) |
| --- | --- |
| DPS + TS | 36.54 |
| DPS | 31.31 |
| DPdS | 26.67 |

TABLE 4

| Core Dopant | Attenuation (dB/m) |
| --- | --- |
| DPS + TS | 117.09 |
| DPS | 98.89 |
| DPdS | 87.12 |

It can be seen that for single mode fibres operating at a wavelength of 870 nm and 1550 nm respectively, the attenuation reduces significantly. The attenuation reduces by as much as 14% at 870 nm and 16% at 1550 nm, when using DPS alone as the dopant material, in comparison with DPS+TS. This improvement is even more marked when DPdS is used as the sole dopant material, with a reduction in attenuation of 27% being observed at 870 nm and a reduction of 26% at 1550 nm.

In general, fibres with higher concentration of core dopant exhibits higher losses, thus there is a trade-off between photosensitivity and transmission loss. Whilst the single dopant materials demonstrated much better reduction in attenuation when compared with DPS+TS, it is envisaged that the attenuation can be reduced significantly further by conducting the preform fabrication in an all-closed environment.

The grating inscription setup involves a beam shutter being placed in the optical path and controlled with a shutter controller, allowing a minimum irradiation time of 7 ms. A beam expander to expand the beam is mounted between the third and fourth mirror giving a 12 mm long elliptical beam on the V-groove. During FBG fabrication, the POF is secured in the V-groove with adhesive tape that limits the FBG length to 10 mm. The optical power of the UV beam after the plano-convex lens was measured to be about 25.5 mW (using Thorlabs S120VC). The same optical output power was used to inscribe all the FBGs presented in this work. This inscription method offers two main advantages: 1) shorten the FBG inscription time; and 2) irradiating the whole phase mask at once. This irradiation scheme uses low power density to illuminate the fibre and was demonstrated to be sufficient to write good quality FBG in just 7 ms. FIG. 3 shows the spectra recorded 10 s, 1 h and 14 days after UV irradiation for FBGs written in 10 s, 1 s, 0.3 s, 0.2 s, 50 ms and 7 ms.

The interesting behaviour observed from FIG. 2a is that all the FBGs appear nearly immediately after UV irradiation. Obviously, the most important information in FIG. 2a is the fabrication of the millisecond FBGs, where 50 ms and 7 ms FBGs exhibited SNR of respectively 12 dB and 7 dB, 10 s after UV irradiation. In FIGS. 2b and 2c, significant growth of all the FBGs was observed. The SNR of 50 ms and 7 ms FBGs were recorded to grow to 18.5 dB and 14.8 dB, 14 days after the UV irradiation process. Moreover, the FBG written with a UV irradiation time of 0.3 s or longer exhibited a noise level higher than FBGs inscribed in less than 0.3 s. This phenomenon is due to the effect of the Norrish type II photochemical reaction, where crosslinking of the PMMA side chains was dominant, which caused irregularities along the irradiated regions along the FBGs.

It is also to be noted that the reflectivity of the FBGs written with a longer UV irradiation time stabilised faster. Furthermore, the FWHM (Full Width Half Maximum) of the FBGs increases with the irradiation time except for FBG written in 0.3 s or less where the FWHM was measured to be 80 pm, 14 days after the inscription. Furthermore, the low side lobes of the millisecond FBGs (especially 7 ms and 50 ms), produce a high SNR, which is desirable for sensing application.

Stability of the Gratings

Gratings written in polymer fibres can be unstable, and their peak wavelength and power can fluctuate over time. Stress in POFs is induced during the fibre drawing process. The stress can be released slowly by thermal annealing at about 80° C. for many hours. Without thermal annealing after FBG fabrication, the fluctuations of the reflection peak wavelength and peak power of the FBGs were recorded for gratings left in an air-conditioned laboratory. FIG. 3 shows the result for gratings left in the environment without strict control of temperature or humidity for up to two week. For all the gratings, the data referred as Day 0 were taken 30 s after the end of irradiation.

Significant fluctuations of the peak power and wavelength were observed during the first few days after inscription. All FBGs stabilised after about 1 week, and the exhibited growth is quite pronounced even for the 7 ms grating. FIGS. 3a and 3b demonstrate that there are two types of growth behaviour which are actually related to the irradiation time and involved two different chemical processes. For longer UV irradiation time (1 s and 10 s), an overall peak power growth is noticeable within one week although a sharp decay is observed within the first few days after fabrication (FIG. 3a), due to damage in the PMMA main chain. For FBGs fabricated with a shorter irradiation time, such as 0.2 s, 50 ms and 7 ms (FIG. 3b), the gratings growth follow a similar trend and the stabilisation is inversely proportional to the UV fluence.

The inset in the upper right corner of FIG. 3b shows the refractive index profile of DPdS-doped fibre both with and without 4 s of UV-irradiation.

Further evidence of these different growth behaviours due to the two different chemical processes is the stabilised peak power after 2 weeks, where 1 s and 10 s FBGs stabilised at greater than −32 dBm whereas the 0.2 s, 50 ms and 7 ms FBGs stabilised around −45 dBm involving a stabilisation of a UV-induced chemical process in the fibre core. An FBG written in 0.3 s (FIG. 3a) exhibited a behaviour produced from the combination of the two chemical processes mentioned above. A sharp growth was observed within the first day, followed by a stable state with a peak power recorded at around −35 dBm. The inset of FIG. 3b shows the measured positive UV induced refractive index change in the DPdS-core fibre doped which was irradiated for 4 s.

To further characterise the stability of the FBGs, thermal tests were conducted using an environmental chamber where the FBGs were cycled with temperature profile over the range of 20 to 50° C. for 10 cycles of 8 hours each, at a constant humidity of 20%. FIGS. 4a, 4b, 4c and 4d show the results of the stabilized FBGs inscribed in 10 s, 0.3 s, 50 ms and 7 ms, respectively.

The grating wavelengths shifted to shorter wavelength with temperature which is consistent with previous findings. Interestingly, all the FBGs exhibit a pellucid stability. The observed wavelength drop for all the FBGs within the first 2 hours is due to the decrease of humidity from ambient air to 20% while temperature was stabilised at 20° C. Furthermore, the FBGs exhibited excellent thermal response and their average sensitivity during the three last cycles (8th, 9th and 10th) were −55 pm/° C. for 0.3 s and 50 ms, and −40 pm/° C. for 10 s and 7 ms FBG. The difference in sensitivity or temperature coefficient is mainly due to the non-uniform doping concentration of DPdS in the fibre core. The test results demonstrated that the use of DPdS as a single material dopant in POF not only permit rapid fabrication of FBGs but also possess excellent properties for potential application as single-use medical sensors.

It can therefore be seen that the use of a single dopant material, exemplified here with DPdS, enables the increase of the refractive-index of polymer optical fibres and their photosensitivity, allowing rapid FBG inscription in just 7 ms, which is more than 60,000 times faster than has previously been reported result in the writing of FBGs in any kinds of POFs at the 325 nm wavelength. These POFs are able to be used in the production of 3D polymer optical fibres with an integrated light source and sensor, with high quality gratings in POFs to be produced during the fibre drawing process.

With reference to FIG. 10, it is envisaged that the use of a single dopant material, exemplified here with DPdS, enables rapid waveguide fabrication of planar photonic devices, in addition to POFs. The use of a single dopant such as DPS or DPdS permits the writing of photonic devices using a UV laser beam on a thin-layer of DPS or DPdS film supported by a substrate of PMMA without any chemical post-processing.

It is of course to be understood that the present invention is not intended to be restricted to the foregoing examples which are described by way of example only.

The invention claimed is:

1. A polymer optical fibre comprising a single dopant material resulting in both a refractive index increase upon UV irradiation and a photosensitivity enhancement during Fibre Bragg grating (FBG) fabrication, wherein the single dopant material comprises at least two phenyl rings linked by a disulfide bridge.

2. A polymer optical fibre as claimed in claim 1, wherein the one or more of the phenyl rings may be functionalized with one or more groups selected from alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, nitro, amino, alkoxy, substituted alkoxy groups, or carboxylic acid groups, or combinations of any two or more thereof.

3. A polymer optical fibre as claimed in claim 1, wherein the single dopant material is a compound selected from the group consisting of:

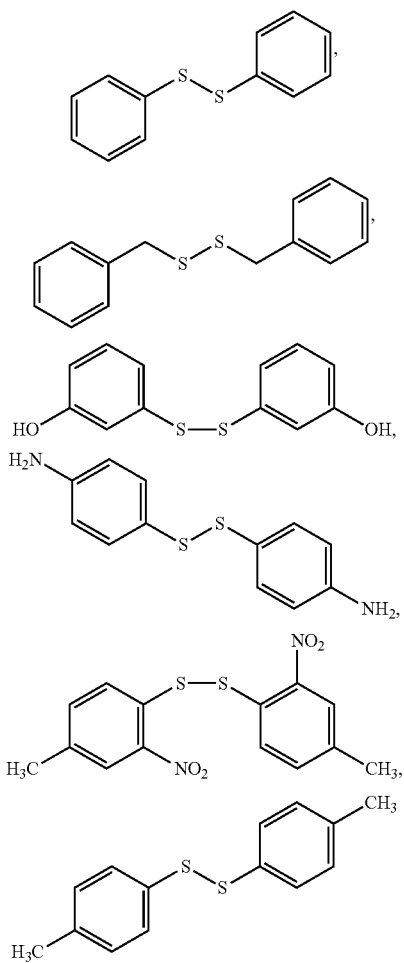

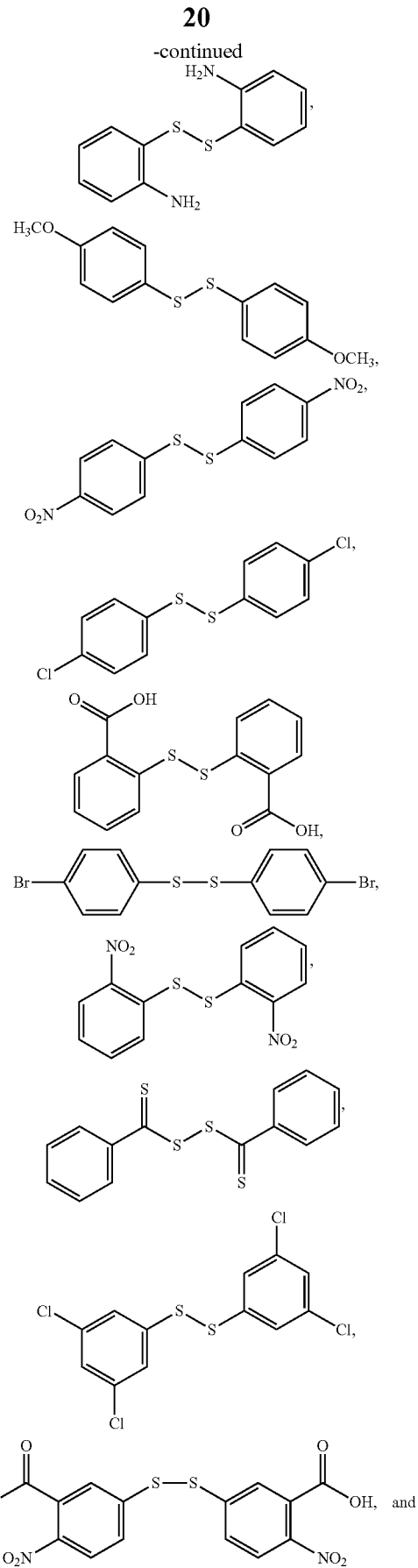

-continued

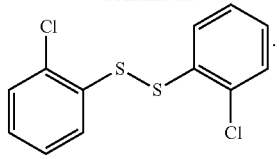

4. A polymer optical fibre as claimed in claim 3, wherein the single dopant material is diphenyl disulfide.

5. A polymer optical fibre as claimed in claim 1, comprising alternating integrated light source sections and sensing sections.

6. A polymer optical fibre as claimed in claim 5, wherein the integrated light source sections are doped with a laser dye and the sensing sections are doped with the single dopant material.

7. A polymer optical fibre as claimed in claim 1, wherein between about 0.1 to about 10 mol % of the single dopant material is employed.

8. A sensor system comprising a polymer optical fibre according to claim 1.

9. A sensor system as claimed in claim 8, wherein the sensor system is a medical sensor system.

10. A method of measuring one or more physical, physiological or biomedical variables, comprising using a sensor system according to claim 9.

11. A method of manufacturing a polymer optical fibre according to claim 1, comprising the steps of:
   doping a polymer optical fibre with a single dopant material, without UV irradiation wherein the single dopant material comprises at least two phenyl rings linked by a disulfide bridge.

12. A method according to claim 11, further comprising the step of:
   inserting the doped polymer optical fibre through an opening in a pre-made polymer preform cladding to form a preform.

13. A method according to claim 12, further comprising the step of:
   drawing the preform into a photosensitive polymer optical fibre.

14. A method as claimed in claim 13 further comprising the step of:
   exposing the photosensitive polymer optical fibre to UV radiation to fabricate a fibre Bragg grating.

15. A method according to claim 14, wherein the polymer optical fibre is exposed to UV radiation from a 325 nm laser for less than 1 second to fabricate a fibre Bragg grating.

16. A method as claimed in claim 13, wherein the polymer optical fibre is a single mode polymer optical fibre.

* * * * *